United States Patent [19]
Horodysky et al.

[11] 4,382,869
[45] May 10, 1983

[54] FRICTION REDUCING AND CORROSION INHIBITING LUBRICANT ADDITIVES AND THEIR COMPOSITIONS

[75] Inventors: Andrew G. Horodysky, Cherry Hill; Phillip S. Landis, Woodbury; Robert M. Gemmill, Jr., Pitman, all of N.J.

[73] Assignee: Mobil Oil Corporation, New York, N.Y.

[21] Appl. No.: 274,839

[22] Filed: Jun. 18, 1981

[51] Int. Cl.³ .............................................. C10M 1/38
[52] U.S. Cl. .................................. 252/47.5; 252/49.6; 548/110; 548/138; 548/141; 548/142
[58] Field of Search ............................ 252/47.5, 49.6; 548/110, 138, 141, 142

[56] References Cited

U.S. PATENT DOCUMENTS

| 2,760,933 | 8/1956 | Fields et al. | 252/47.5 X |
| 2,799,652 | 7/1957 | Fields | 252/47.5 X |
| 2,836,564 | 5/1958 | Roberts et al. | 252/47.5 |
| 2,850,453 | 9/1958 | Fields | 252/47.5 X |
| 4,193,882 | 3/1980 | Gemmill, Jr. | 252/47.5 |
| 4,301,019 | 11/1981 | Horodysky et al. | 252/47.5 X |

Primary Examiner—Andrew Metz
Attorney, Agent, or Firm—M. G. Gilman; C. J. Speciale; C. E. Setliff

[57] ABSTRACT

Dimercaptothiadiazole adducts of hydroxyl-containing unsaturated compounds and their borated analogues provide effective multifunctional friction reducing and corrosion inhibiting properties to various lubricating fluids when incorporated therein.

19 Claims, No Drawings

FRICTION REDUCING AND CORROSION INHIBITING LUBRICANT ADDITIVES AND THEIR COMPOSITIONS

BACKGROUND OF THE INVENTION

1. Field of the Invention

This invention is based upon the discovery that adducts of hydroxyl-containing and borated adducts of hydroxyl-containing unsaturated alcohols are multifunctional lubricant additives which effectively reduce friction and inhibit corrosion when incorporated into oils of lubricating viscosity.

2. Description of the Prior Art

In view of the current energy crisis and the possibility of future oil embargoes, there is a continual need for improving means of reducing energy requirements in general and more specifically energy requirements of internal combustion engines which consume huge quantities of energy. Some efforts towards solving or at least improving this situation have been purely mechanical and others have been directed towards improved lubricants.

For example, reaction products containing the mercapto-1,3,4-thiadiazole structure have found widespread use as lubricant antioxidants and metal passivators. The compositions and utility of the adducts described in this patent application, however, are believed to be novel. Adducts of functionalized unsaturates and mercaptothiadiazoles have not been used to applicants' knowledge as friction reducing compositions in lubricants.

Accordingly, so far as is known, there have been no efforts to use mercaptothiadiazole adducts of hydroxyl-containing unsaturated compounds or borated hydroxyl-containing compounds as lube additives. However, U.S. Pat. No. 4,193,882 discloses lubricant compositions containing the reaction product of said 2,5-dimercapto-1,3,4-thiazole and oleic acid which inhibit metal corrosion.

SUMMARY OF THE INVENTION

The present invention is directed to novel adducts of hydroxyl-containing unsaturated compounds and to borated adducts of hydroxyl-containing unsaturated compounds. More specifically, the invention is directed to reaction products of mercaptothiadiazoles with hydroxyl-containing or borated hydroxyl-containing unsaturated compounds such as oleyl alcohol which have been found to be effective multifunctional friction reducing and corrosion inhibiting additives when evaluated in lubricating oils. These sulfur, nitrogen and oxygen containing compositions, when used in additive concentrations of up to 4% weight in a fully formulated SAE 5W-20 automotive engine oil, impart friction reducing characteristics as demonstrated in the Low Velocity Friction Apparatus (LVFA) test. The thiadiazole moiety is believed to impart metal deactivating and/or antioxidant properties to these compositions. This invention is further directed to a method of reducing friction in internal combustion engines and improving inhibition to corrosion of such engines.

DESCRIPTION OF THE PREFERRED EMBODIMENTS

Dimercaptothiadiazole adducts of hydroxylcontaining and borated hydroxyl-containing unsaturated compounds are highly effective friction reducing and corrosion inhibiting additives for lubricants. The present invention minimizes friction losses and thereby decreases fuel consumption employing these adducts, or mixtures of these adducts, as lubricating components of lubricating oils. The products of the present invention are also relatively non-corrosive to copper and can serve to improve the copper strip corrosivity of normally corrosive lubricants.

Typical unsaturated alcohols contemplated for use in this invention include any alcohols of the formula:

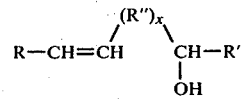

where R and R' may be the same or different and can be hydrogen or straight or branched chain alkyl, alkenyl, cycloalkyl, cycloalkenyl, alkynyl, aryl or alkaryl. R" can be a hydrocarbyl group such as a methylene ($CH_2$) group containing from 1 to 15 carbon atoms and x is zero or 1. Alternatively, R" can be zero and contain no carbon atoms. R, R' and R" usually contain from 1 to about 30 carbon atoms. Among the preferred unsaturated alcohols is oleyl alcohol.

At least one or more olefinic groups must be present in the hydroxyl-containing compound or borated hydroxyl-containing compound. More are permissible. A hydrocarbyl chain may contain two or more olefinic groups. The alcohols can be obtained commercially or made by any of many methods well known in the art.

Without limiting the hydroxyl-containing unsaturated compounds of the present invention, the following are mentioned merely as exemplary: oleyl alcohol, linoleyl alcohol, deceneols such as 2-decene-5-ol, dodeceneols such as 4-dodecene-1-ol, hexadeceneols such as 9-hexadecene-1-ol, cyclohexene-3-ol, cyclooctene-3-ol, etc. The several tetradeceneols and hexadeceneols can also be used. Sulfur may also be found on the hydrocarbyl group of the unsaturated alcohol as a sulfide or polysulfide linkage.

The borated products of the present invention are produced by the reaction of the unsaturated alcohol with boric acid in a suitable solvent or solvents such as toluene, xylene, or reactive solvents, at temperatures ranging from about 90° C. to about 250° C. to yield products containing at least 0.01% or more of boron. Specific reaction conditions and molar equivalents of the reactants are well known in the art. Partial or complete boration can be used to impart the beneficial characteristics. In carrying out the reaction, an excess of a boron-containing borating reagent can be used for more complete boration which is generally preferred. Boration is not limited to the boric acid method, however, and any convenient method of boration known to the art may be used.

For example, transesterification using a trialkyl borate such as tributyl borate at reaction temperatures up to 270° C. can be used. Broadly, also useful are the alkyl borates of the formula

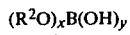

wherein $R^2$ is a $C_1$–$C_6$ alkyl group, x is 1 to 3 and y is 0 to 2, and $x+y=3$.

In carrying out the reaction to form the boron product, up to stoichiometric amounts of the hydroxy unsaturated compound and boron compound may be used. That is, for every one mole of boron compound, one may use up to an amount of the unsaturated alcohol which will contain an equivalent amount of hydroxyl functions. The temperature of reaction can vary over the range of from about 75° C. to about 270° C., preferably from about 100° C. to about 200° C.

While atmospheric pressure is generally preferred, the reaction with the boron compound can be advantageously run at from about 0.3 to about 2 atmospheres. Furthermore, a solvent is desirable. In general, any polar or non-polar, unreactive solvent can be used, including toluene, xylene, 1,4-dioxane or reactive solvents such as butanol, pentanols, etc. Times for completing the reaction will range from 1 to 20 hours.

Some of the thiadiazoles useful in the practice of this invention are more particularly called mercaptothiadiazoles, and can include, 2,5-dimercapto-1,3,4-thiadiazole and have the formula:

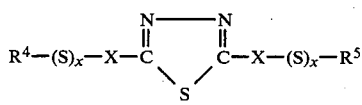

wherein $R^4$ and $R^5$ are hydrogen or hydrocarbyl groups, containing from 1 to 30 carbon atoms, x is to 0 to 3 and X is nitrogen or sulfur, one of which must be sulfur. The hydrocarbyl groups can be alkyl, aryl, alkenyl alkaryl or aralkyl, preferably alkyl, and specifically include methyl, butyl, octyl, decyl, dodecyl, octadecyl, phenyl, tolyl, benzyl, and the like. One of $R^4$ and $R^5$ must be hydrogen. They can be made in accordance with the method described in U.S. Pat. No. 2,719,125, which is incorporated herein by reference. It may also be purchased from commercial sources.

The mercaptothiadiazoles useful herein also include amino derivatives such as 2-amino-5-mercapto-1,3,4-thiadiazole

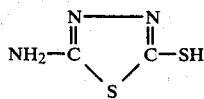

The synthesis and structure of the mercaptothiadiazole hydroxyl-containing unsaturated compounds may be depicted by the following equations

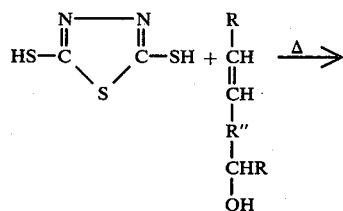

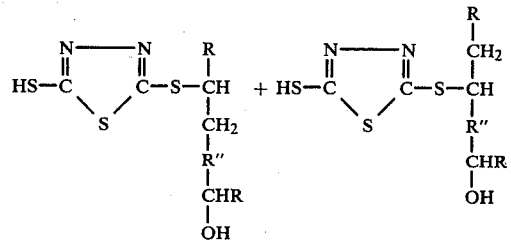

if molar amounts of unsaturated alcohols to mercaptothiadiazole are used.

In the case of dimercaptothiadiazoles, both mercapto groups can react with two moles of unsaturated alcohols to form the following structures

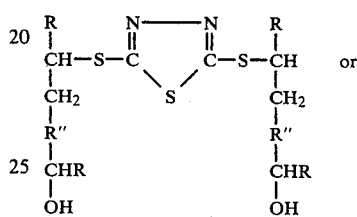

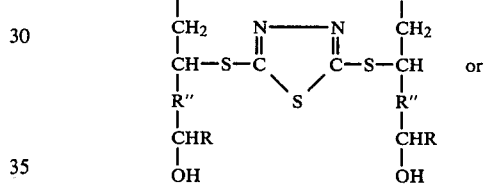

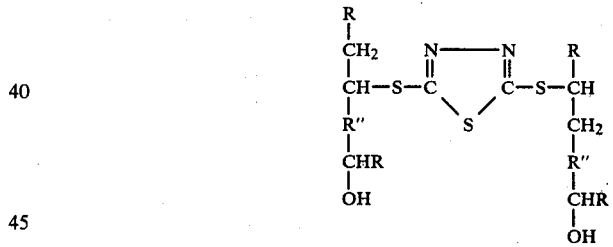

and mixtures of all of the above structures depending primarily on the ratio of unsaturated alcohol or borated unsaturated alcohol to mercaptothiadiazolel used. Mixtures of hydroxyl-containing unsaturated alcohols can also be used as can mixtures of borated unsaturated alcohols and mixtures of both borated and non-borated unsaturated alcohols.

Statistical mixtures including products derived from the reaction of more than one olefin group per molecule are possible. The reaction of both mercapto groups of 2,5-dimercapto-1,3,4-thiadiazole is also quite possible and is dependent primarily upon the molar ratio of the reactants used. Thus, although we believe the reactions as indicated predominate, other reactions are possible. We do not wish to be bound to the chemistry shown since other products may form in lesser amounts.

The above general equations and considerations are equally valid with respect to the reaction of mercaptothiadiazoles with borated hydroxyl-containing unsaturated alcohols, mixtures of borated hydroxyl-containing unsaturated compounds, mixtures of hydroxyl-containing unsaturated compounds and borated hydroxyl-containing unsaturated compounds.

Reaction temperatures may range from about 140° C. to about 200° C. The pressure is usually atmospheric, but lighter pressure may be used, if desired or higher pressures can be used. An inert gas purge is often used to minimize possible decomposition.

Equimolar amounts of reactants are generally used. However, the molar ratio of hydroxyl-containing or borated hydroxyl-containing unsaturated compound to mercaptothiadiazole may vary from more than 2:1 to less than 1:1. A large excess of hydroxyl-containing or borated hydroxyl-containing unsaturated alcohol can be also used with molar ratios in excess of two-fold. Although this reaction is generally carried out at elevated temperatures, acid catalysts or peroxide catalysts may be used to effect the reaction at lower temperatures. Hydrocarbon solvents could be optionally used, but are not required.

The boron compound can be used in amounts stoichiometric to the hydroxyl present in the hydroxyl-containing unsaturated compound or, if preferred, less than stoichiometric amounts can be used so free hydroxyl groups are present in the final product.

The additives may be used effectively to impart to organic media, particularly to greases and lubricating oils and fuels, the properties mentioned hereinabove. An effective amount of the additive compound will range from about 0.1% to about 10% by weight. Preferably, the organic medium or substrate, e.g., oil of lubricating viscosity or grease therefrom, contains from about 1.0% to 5.0% of the additive and more preferably from about 2.0% to about 4.0% by weight thereof, based on the total weight of the lubricant composition. In hydrocarbon fuels, 0.00001% to 0.1% can be used to impart beneficial properties and preferably 0.0001 to 0.01 wt.%.

Of particular significance, in accordance with the present invention, is the ability to improve the resistance to oxidation and corrosion of oleaginous materials such as lubricating media which may comprise liquid oils, in the form of either a mineral oil or a synthetic oil, or mixtures thereof, or in the form of a grease in which any of the aforementioned oils are employed as a vehicle. In general, mineral oils, both paraffinic, naphthenic and mixtures thereof, employed as the lubricant, or grease vehicle, may be of any suitable lubricating viscosity range, as for example, from about 45 SUS at 100° F. to about 600 SUS at 100° F., and preferably, from about 40 SUS to about 250 SUS at 210° F. These oils may have viscosity indexes ranging to about 100 or higher. Viscosity indexes from about 70 to about 95 are preferred. The average molecular weights of these oils may range from about 250 to 800.

Where the lubricant is to be employed in the form of a grease, the lubricating oil is generally employed in an amount sufficient to balance the total grease composition, after accounting for the desired quantity of the thickening agent and other additive components to be included in the grease formulation. A wide variety of materials may be employed as thickening or gelling agents. These may include any of the conventional metal salts or soaps, which are dispersed in the lubricating vehicle in grease-forming quantities in such degree as to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other aspects, any materials which are normally employed for thickening or gelling hydrocarbon fluids for forming grease can be used in preparing the aforementioned improved grease in accordance with the present invention. This invention can be used in addition to antiwear, extreme pressure, dispersant, detergent, pour depressant, antifoam and viscosity improving additives and the like in fully formulated lubricant formulations, along with additives such as sulfonates, phenates succinimides, phosphorodithioates and the like without detracting from the invention.

In instances where synthetic oils, or synthetic oils employed as the vehicle for the grease, are desired in preference to mineral oils, or in combination therewith, various compounds of this type may be successfully utilized. These synthetic oils may be used alone, in combination with mineral oils, or with each other as a lubricating oil. Typical synthetic vehicles include synthetic hydrocarbons such as polyisobutylene, polybutenes, hydrogenated polydecenes, the polyglycols, including polypropylene glycol, polyethylene glycol, synthetic ester oils illustrated by trimethylolpropane esters, neopentyl alcohol and pentaerythritol esters, di(2-ethylhexyl)sebacate, di(2-ethylhexyl)adipate, dibutyl phthalate and other types, as for example, fluorocarbons, esters of phosphorus-containing acids, liquid ureas, ferrocene derivatives, hydrogenated synthetic oils, chain-type polyphenols, siloxanes and silicones (polysiloxanes), alkyl-substituted diphenyl esters typified by a butyl substituted bis(p-phenoxyphenyl)ether and phenoxyphenyl ether.

Having described the invention broadly, the following are offered as specific illustrations. They are illustrative only and are not intended to limit the invention.

EXAMPLE 1

Oleyl Alcohol-Dimercaptothiadiazole Adduct

Approximately 550 g of oleyl alcohol and 100 g of 2,5-dimercapto-1,3,4-thiadiazole were charged to a stirred reactor and heated at 180°–185° C. for 4 hours under a nitrogen atmosphere. The product was cooled to 100° C. and filtered through diatomaceous earth. The product was a clear fluid and contained:
 2.6% nitrogen
 8.0% sulfur
 71.1% carbon
 12.4% hydrogen

EXAMPLE 2

Trioleyl Borate-Dimercaptothiadiazole Adduct

Approximately 270 g of trioleyl borate (made by the reaction of oleyl alcohol with boric acid) and 26 g of 2,5-dimercapto-1,3,4-thiadiazole were charged to a stirred reactor and heated at 180° C. for 4½ hours under a nitrogen atmosphere. The product was cooled to 100° C. and filtered through diatomaceous earth. The product was a clear fluid and contained:
 1.0% nitrogen
 3.6% sulfur
 74.3% carbon
 12.4% hydrogen

EXAMPLE 3

Oleyl Alcohol-Dimercaptothiadiazole Adducts

Approximately 1100 g of oleyl alcohol and 200 g of 2,5-dimercapto-1,3,4-thiadiazole were charged to a stirred reactor and heated to 175°–185° C. for about 4 hours under a nitrogen atmosphere. The product was cooled to about 70° C. and filtered through diatomaceous earth. The product was a clear fluid and contained:

2.7% nitrogen
7.8% sulfur
70.4% carbon
11.5% hydrogen

Examples 1 and 2 described above were blended into a fully formulated SAE 5W-20 automotive engine oil containing detergent/disposant and inhibitor package and evaluated using the Low Velocity Friction Apparatus. General characteristics of the oil were: KV@100° C.-6.8 cs; KV@40° C.-36.9 cs; and VI-143.

Low Velocity Friction Apparatus (LVFA)

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever cam-motor arrangement.

Procedure

The rubbing surfaces and 12–13 ml. of test lubricant are placed on the LVFA. A 240 psi load is applied, and the sliding speed is maintained at 40 fpm at ambient temperature for a few minutes. A plot of coefficients of friction ($U_k$) over a range of sliding speeds, 5 to 40 fpm (25–195 rpm), is obtained. A minimum of three measurements is obtained for each test lubricant. Then, the test lubricant and specimens are heated to 250° F., another set of measurements is obtained, and the system is run for 50 minutes at 250° F., 500 psi, and 40 fpm sliding speed. Freshly polished steel specimens are used for each run. The surface of the steel is parallel ground to 4 to 8 microinches. The percentages by weight are percentages by weight of the total lubricating oil composition, including the usual additive package. The data are percent decrease in friction according to:

$$\frac{(U_k \text{ of oil alone}) - (U_k \text{ of additive plus oil}) \times 100}{(U_k \text{ of oil alone})}$$

The value for the oil alone would be zero as shown in the table below.

Table 1 summarizes the results.

TABLE 1

FRICTION REDUCTION TEST RESULTS

| Example | Additive Conc. Wt. % | Percent Change in Coefficient of Friction | |
|---|---|---|---|
| | | 5 Ft./Min. | 30 Ft./Min. |
| Base Blend | — | 0 | 0 |
| 1 | 4 | 17 | 38 |
| 2 | 4 | 16 | 11 |
| | 2 | 17 | 10 |

Examples 2 and 3 described above were blended into 200 second solvent paraffinic neutral lubricating oil and evaluated for copper corrosivity characteristics. Good control of copper corrosion was demonstrated by these novel compositions.

TABLE 2

COPPER STRIP CORROSIVITY TEST RESULTS USING ASTM D130-80

| Example | Additive Conc., Wt. % | ASTM D130-80 210° F., 6 Hours | ASTM D130-80 250° F., 3 Hours |
|---|---|---|---|
| 2 | 1 | 2A | 1B |
| | 3 | 1B | 1B |
| 3 | 1 | 2A | 1B |
| | 3 | 1B | 1B |

Dimercaptothiadiazole adducts of hydroxyl-containing and borated hydroxyl-containing unsaturated compounds and related compositions improve the gasoline fuel economy of automotive engine oils and improve the fuel and/or energy efficiency of a variety of other automotive and industrial lubricants and hydrocarbon fuels. The non-metallic compositions described are oil soluble, essentially odorless friction reducing additives which are useful at low additive concentrations. These compositions do not contain any potentially undesirable phosphorus or metallic salts, but exhibit additional antioxidation and/or potential bearing corrosion inhibiting properties. The use of effective fuel economy improving additives aids in efforts to reduce fuel dependency.

Examples 1 and 3 described hereinabove were blended to a 200" solvent paraffinic neutral lubricating oil and evaluated for oxidative stability using the Catalytic Oxidation Test at 325° F. for 40 hours.

| CATALYTIC OXIDATION TEST | | | |
|---|---|---|---|
| | Additive Conc. Wt. % | Lead Loss, mg | % Increase in Viscosity of Oxidized Oil Using KV @ 210° F. | Neutralization Number of Oxidized Oil |
| Base oil 0% Additive, 200" Solvent Paraffinic Neutral Lubricating Oil | — | −1.2 | 67 | 3.62 |
| Example 1 | 1 | −1.4 | 34 | 2.67 |
| Example 3 | 1 | −0.6 | 32 | 2.61 |

In most cases there was significant improvement in oxidation stability over the base oil. Basically, the test lubricant is subjected to a stream of air which is bubbled through at a rate of 5 liters per hour and 325° F. for 40 hours. Present are samples of metals commonly used in engine construction such as iron, copper, aluminum and lead. See U.S. Pat. No. 3,682,980 herein incorporated by reference in its entirety for more complete details of the test. Improvement in viscosity increase, or neutralization number show control of oxidation.

We claim:

1. A product of reaction obtained by reacting a hydroxyl-containing unsaturated compound or a borated derivative thereof, the borated derivative being prepared at a temperature of from about 75° C. to about 270° C. using up to stoichiometric amounts of unsaturated compound and boron compound with a mercaptothiadiazole, at a temperature of from about 140° C. to about 200° C. using a ratio of unsaturated compound or borated derivative to mercaptothiadiazole of less than 1:1 to more than 2:1, and wherein said unsaturated compound has the formula

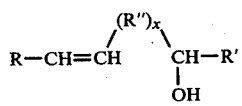

wherein R and R' are the same or different and are hydrogen, a straight chain alkyl, a branched chain alkyl, alkenyl, cycloalkyl, cycloalkenyl, alkyryl, aryl or alkaryl and contain from 1 to 30 carbon atoms, R" is a hydrocarbyl group containing from 1 to 15 carbon atoms and x is zero or 1.

2. The product of claim 1 wherein the boron compound used for boration has the formula

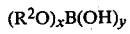

wherein $R^2$ is a $C_1$-$C_6$ alkyl group, x is 1 to 3 and y is 0 to 2 and x+y must equal 3.

3. The product of claim 1 wherein the mercaptothiadiazole has the formula:

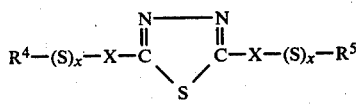

wherein $R^4$ and $R^5$ are hydrogen or hydrocarbyl groups containing from 1 to about 30 carbon atoms, x is 0 to 3 and X is nitrogen or sulfur, and wherein either $R^4$ or $R^5$ must be hydrogen and at least one X must be sulfur.

4. The product of claim 3 wherein said hydrocarbyl groups are alkyl, aryl, cycloalkyl, alkaryl or aralkyl groups.

5. The product of claim 1 obtained by reacting oleyl alcohol with 2,5-dimercapto-1,3,4-thiadiazole.

6. The product of claim 1 obtained by reacting borated oleyl alcohol with 2,5-dimercapto-1,3,4-thiadiazole.

7. The product of claim 1 wherein boration is with boric acid.

8. A lubricant composition containing a major portion of a lubricating oil or a grease prepared therefrom and a minor friction reducing or corrosion inhibiting amount of a product of reaction obtained by reacting a hydroxyl-containing unsaturated compound or a borated derivative thereof, the borated derivative being prepared at a temperature of from about 75° C. to about 270° C. using up to stoichiometric amounts of unsaturated compound and boron compound with a mercaptothiadiazole, at a temperature of from about 140° C. to about 200° C. using a ratio of unsaturated compound or borated derivative to mercaptothiadiazole of less than 1:1 to more than 2:1, and wherein said unsaturated compound has the formula

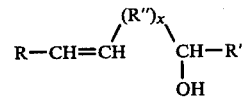

wherein R and R' are the same or different and are hydrogen, a straight chain alkyl, a branched chain alkyl, alkenyl, cycloalkyl, cycloalkenyl, alkyryl, aryl or alkaryl and contain from 1 to 30 carbon atoms, R" is a hydrocarbyl group containing from 1 to 15 carbon atoms and x is zero or 1.

9. The composition of claim 8 wherein in preparing said product the boron compound used for boration has the formula

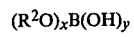

wherein $R^2$ is a $C_1$-$C_6$ alkyl group, x is 1 to 3 and y is 0 to 2 and x+y=3.

10. The composition of claim 8 wherein in preparing said product, the mercaptothiadiazole has the general formula

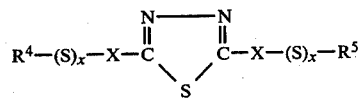

wherein $R^4$ and $R^5$ are hydrogen or hydrocarbyl groups containing from 1 to 30 carbon atoms, x is 0 to 3 and X is nitrogen or sulfur, and wherein either $R^4$ or $R^5$ must be hydrogen and at least one X must be sulfur.

11. The composition of claim 10 wherein said hydrocarbyl groups are alkyl, cycloalkyl, aryl, alkaryl, or aralkyl groups.

12. The composition of claim 8 wherein said product is prepared by reacting oleyl alcohol with 2,5-dimercapto-1,3,4-thiadiazole.

13. The composition of claim 8 wherein said product is prepared by reacting borated oleyl alcohol with 2,5-dimercapto-1,3,4-thiadiazole.

14. The composition of claim 9 wherein boration is with boric acid.

15. The composition of claim 8 wherein said lubricant is a mineral oil.

16. The composition of claim 8 wherein said lubricant is a synthetic oil.

17. The composition of claim 8 wherein said lubricant is a mixture of mineral and synthetic oils.

18. The composition of claim 8 wherein said lubricant is a grease prepared from a mineral oil, a synthetic oil or a mixture thereof.

19. A method of reducing friction in an internal combustion engine by treating the moving parts of said engine with a lubricating oil or a grease prepared therefrom containing a minor effective amount of a friction reducing or corrosion inhibiting product obtained by reacting a hydroxyl-containing unsaturated compound or a borated derivative thereof, the borated derivative being prepared at a temperature of from about 75° C. to about 270° C. using up to stoichiometric amounts of unsaturated compound and boron compound with a mercaptothiadiazole, at a temperature of from about 140° C. to about 200° C. using a ratio of unsaturated compound or borated derivative to mercaptothiadiazole of less than 1:1 to more than 2:1, and wherein said unsaturated compound has the formula

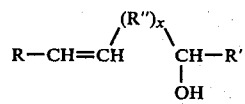

wherein R and R' are the same or different and are hydrogen, a straight chain alkyl, a branched chain alkyl, alkenyl, cycloalkyl, cycloalkenyl, alkyryl, aryl or alkaryl and contain from 1 to 30 carbon atoms, R" is hydrocarbyl group containing from 1 to 15 carbon atoms and x is zero or 1.

* * * * *